United States Patent
Roa Engel et al.

(10) Patent No.: US 10,265,641 B2
(45) Date of Patent: Apr. 23, 2019

(54) SIMULTANEOUS RECOVERY OF ORGANIC COMPOUNDS AND EXTRACTANTS

(71) Applicant: NEDERLANDSE ORGANISATIE VOOR TOEGEPAST-NATUURWETENS CHAPPELIJK ONDERZOEK TNO, 's-Gravenhage (NL)

(72) Inventors: Carol Andrea Roa Engel, 's-Gravenhage (NL); Jan Harm Urbanus, 's-Gravenhage (NL); Dirk Verdoes, 's-Gravenhage (NL)

(73) Assignee: NEDERLANDSE ORGANISATIE VOOR TOEGEPAST-NATUURWETENS CHAPPELIJK ONDERZOEK TNO, 's-Gravenhage (NL)

( * ) Notice: Subject to any disclaimer, the term of this patent is extended or adjusted under 35 U.S.C. 154(b) by 211 days.

(21) Appl. No.: 15/306,932

(22) PCT Filed: May 1, 2015

(86) PCT No.: PCT/EP2015/059620
§ 371 (c)(1),
(2) Date: Oct. 26, 2016

(87) PCT Pub. No.: WO2015/166098
PCT Pub. Date: Nov. 5, 2015

(65) Prior Publication Data
US 2017/0050119 A1   Feb. 23, 2017

(30) Foreign Application Priority Data
May 1, 2014   (EP) .................................... 14166797

(51) Int. Cl.
*B01D 9/04* (2006.01)
*B01D 9/00* (2006.01)
(Continued)

(52) U.S. Cl.
CPC ............. *B01D 9/04* (2013.01); *B01D 9/0004* (2013.01); *B01D 11/0492* (2013.01); *C02F 1/26* (2013.01);
(Continued)

(58) Field of Classification Search
None
See application file for complete search history.

(56) References Cited

U.S. PATENT DOCUMENTS

| 4,309,564 A | * | 1/1982 | Loncrini | ................. C07C 69/88 560/67 |
| 9,682,908 B2 | * | 6/2017 | Zaher | ...................... C07C 29/86 |
| 2009/0023902 A1 | * | 1/2009 | Frank | ..................... C07K 1/145 530/412 |

FOREIGN PATENT DOCUMENTS

| WO | 2004089503 A1 | 10/2004 |
| WO | 2012/130316 A1 | 10/2012 |

OTHER PUBLICATIONS

Rai, et al., "Solidification behavior of binary organic monotectic alloys," Thermochimica Acta, (1996) p. 209-217 (Year: 1996).*
(Continued)

*Primary Examiner* — Chester T Barry
(74) *Attorney, Agent, or Firm* — Lucas & Mercanti, LLP

(57) ABSTRACT

The invention relates to a method for recovering an organic compound from a feed stream comprising the steps of —extracting the organic compound into an organic solvent, thereby obtaining a mixture of the solvent and the organic compound; and —simultaneously crystallizing the solvent and the organic compound by cooling the mixture; and
(Continued)

—separating the solid organic solvent and solid organic compound.

26 Claims, 3 Drawing Sheets

(51) Int. Cl.
| | | |
|---|---|---|
| *B01D 11/04* | (2006.01) | |
| *C02F 1/26* | (2006.01) | |
| *C07C 29/76* | (2006.01) | |
| *C07C 29/78* | (2006.01) | |
| *C07C 29/86* | (2006.01) | |
| *C07C 51/42* | (2006.01) | |
| *C07C 51/43* | (2006.01) | |
| *C07C 51/48* | (2006.01) | |
| *C07F 9/50* | (2006.01) | |
| *C12P 7/18* | (2006.01) | |
| *C02F 1/52* | (2006.01) | |

(52) U.S. Cl.
CPC .............. *C07C 29/76* (2013.01); *C07C 29/78* (2013.01); *C07C 29/86* (2013.01); *C07C 51/42* (2013.01); *C07C 51/43* (2013.01); *C07C 51/48* (2013.01); *C07F 9/5095* (2013.01); *C12P 7/18* (2013.01); *C02F 2001/5218* (2013.01); *Y02E 50/17* (2013.01)

(56) References Cited

OTHER PUBLICATIONS

Rastogi, et al., "Solid—Liquid Equilibria in Mixtures of Non-Electrolytes," J. Phys. Chem., vol. 62 No. 6 (1958) p. 641-644 (Year: 1958).*

Fichtels, "Binary Eutectic Phase Diagrams," dated Sep. 29, 2000 (2000), downloaded Dec. 19, 2018, http://csmgeo.csm.jmu.edu/geollab/Fichter/IgnRx/BinryEu.html (Year: 2000).*

Sun et al., "Salting-out extraction and crystallization of succinic acid from fermentation broths," Process Biochemistry, vol. 49, No. 3, Jan. 7, 2014, pp. 506-511, XP028637618.

International Search Report for International Application No. PCT/NL2015/050163 dated Aug. 3, 2015 (3 pages).

* cited by examiner

SIMULTANEOUS RECOVERY OF ORGANIC COMPOUNDS AND EXTRACTANTS

CROSS-REFERENCE TO RELATED APPLICATIONS

This application is a 371 of PCT/EP2015/059620, filed May 1, 2015, which claims the benefit of European Patent Application No. 14166797.2, filed May 1, 2014.

FIELD OF THE INVENTION

The invention is directed to a method for recovering an organic compound from a feed stream, such as an aqueous fermentation stream.

BACKGROUND OF THE INVENTION

Due to the continued reduction of petroleum resources, the need to look for alternative resources or feedstocks, process routes and materials has become a scientific aim for the chemical industry. The use of renewable biomass as sustainable resource for the production of bio-fuels and bio-chemicals is expected to grow significantly in the coming decades. This expansion is enabled by the breakthroughs in genomics and industrial biotechnology. The so-called white biotechnology area focuses on alternative production routes for producing organic compounds such as carboxylic acids and alcohols from renewable bio-based feedstocks such as glucose, starch, non-edible oils and fats, woody and agro-food residue streams or organic waste streams containing these feedstocks. The industrial biotechnology makes use of enzymes or micro-organisms to convert the mentioned feedstocks, possibly after a pre-treatment step, into the targeted bio-fuel or bio-chemical. White biotechnology may reduce our dependency on oil and has the additional advantage that such routes are considered as $CO_2$-neutral as $CO_2$ has been captured in the biomass during the growth.

Fermentation is the most dominant technique within the white biotechnology domain. Fermentation is a metabolic process in which organisms like yeast, bacteria or fungi convert feedstocks like sugars, fatty acids or glycerol to products like acids, gases and/or alcohol.

Besides the fermentation product itself, fermentation streams contain large amounts of water and many secondary compounds. This makes the recovery of the desired product often difficult.

A known process that is often used for recovering organic products from a fermentation stream is liquid-liquid extraction. In this process, the organic product (the solute) is extracted from the aqueous fermentation stream into an organic solvent (the extractant), thereby obtaining a mixture mainly comprising the organic fermentation product and the organic solvent (this mixture may be referred to as the extract or enriched solvent). The organic solvent is subsequently regenerated by a back extraction step in which the organic product is transferred to water, thereby obtaining an aqueous product solution and the regenerated organic solvent. The pH of the water stream entering the back-extraction is often adjusted to stimulate the transfer of the organic compound from the solvent to the water stream. The aqueous product solution is then typically purified, e.g. by crystallization. Various methods are known to achieve crystallization, such as adjustment of the pH, cooling or the removal of water by evaporation and/or distillation and or combinations of the aforementioned methods.

A disadvantage of back-extraction is that this step requires high energy or the addition of extra chemicals to successfully transfer the organic solvent back into water. In order for the organic compound to leave the organic solvent and enter the water, the solubility of the organic product in water needs to be enhanced. This may for example be achieved by changing the temperature or the pH of the enriched solvent. However, this will require high energy costs due to heating and/or cooling (in case of changing the temperature) or adding chemicals (in case of adjusting the pH).

A further disadvantage of back-extraction is that the aqueous product solution may get contaminated by the organic solvent. Similarly, a disadvantage of extraction is that the feed stream may get contaminated with organic solvent.

A further disadvantage of back-extraction is that the resulting aqueous solution comprising the organic product will typically be rather diluted and comprises a relatively large amount of water. This water needs to be removed in the down-stream processing.

A further disadvantage is that the organic product may not yet be in the desired form after back-extraction. An illustrative example of the last feature is the back-extraction of organic acids into water with a relatively high pH (i.e. $\gg$pH=7), which results in the conversion of the acid into the corresponding carboxylate during the back extraction. Recovery of the acid from the aqueous product solution will then often require a pH adjustment with an acid to convert the carboxylate back into the targeted acid. Such a procedure does not only lead to high costs for acid and base consumption but also to the production of a salt as a by-product, where the salt is composed of the counter-ions of the used acid and base.

It follows from the above that there is a need to develop short, simple and cheap recovery processes to recover organic products from feed streams, in particular from fermentation streams.

SUMMARY AND OBJECTS OF THE INVENTION

An object of the invention is to recover an organic compound from a feed stream such as an organic product stream originating from a fermentation process in a relatively simple process, which may require only a limited number of operation steps.

A further object of the invention is to provide a liquid-liquid extraction technique with does not suffer from one or more of the above-mentioned disadvantages.

At least one of these objects was met by providing a method for recovering an organic compound from a feed stream comprising the steps of extracting the organic compound from the feed stream into an organic solvent, thereby obtaining a mixture of the solvent and the organic compound; and simultaneously crystallizing the solvent and the organic compound by cooling the mixture; and separating the solid organic solvent and solid organic compound.

The inventors found that when recovering an organic compound from a fermentation stream using liquid-liquid extraction with an organic solvent, the product and solvents can efficiently be recovered from the organic mixture by simultaneous crystallization and subsequent separation of the solid solvent and solid organic compound. The method of the invention has the advantage that the solvent and product can be efficiently recovered, without requiring complex and/or energy consuming downstream processing steps such as back-extraction and/or evaporation and/or consecutive pH-adjustments. Thus, the invention provides for the possibility of recovering the organic fermentation product and the organic solvent from a fermentation stream using a single liquid-liquid extraction step, a single crystallization step and a simple solid-solid separation step.

Although the invention is discussed herein mainly with respect to treating fermentation streams, it will be understood that the invention can in principle be applied to recover organic compounds from any liquid mixture. The invention can in particular be suitably conducted in downstream processing techniques wherein liquid-liquid extraction is used. Examples of such processes are nuclear reprocessing, ore processing, the production of organic chemicals, the production of vegetable oils and biodiesel, treatment of process and waste water streams and increasingly also in the work-up of fermentation broths. Accordingly, the method of the invention may be applied in any of these processes to recover organic products from a feed stream.

DETAILED DESCRIPTIONS

Figure 1:
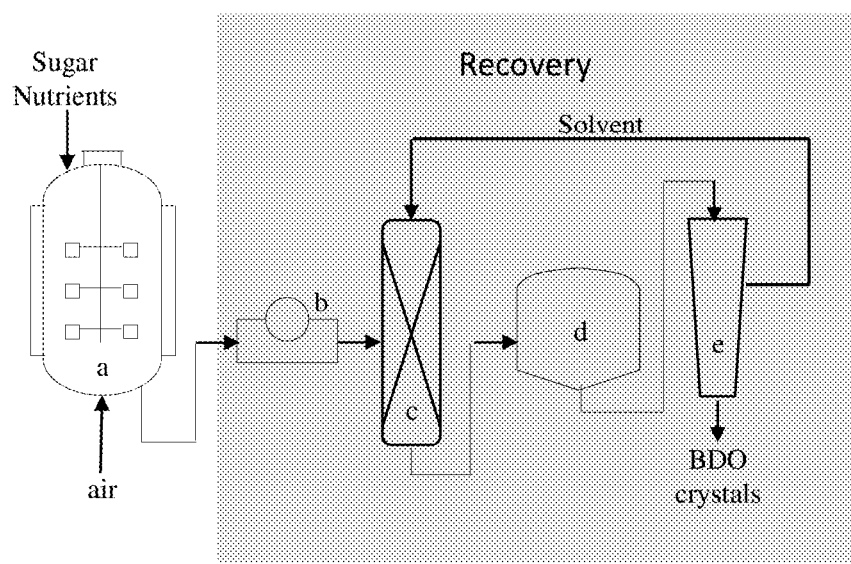
FIG. 1 is a schematic representation of one embodiment of the method of the invention, wherein BDO is recovered from a fermentation reaction. In the schematic representation, the following steps are indicated: (a) fermentation; (b) biomass separation (e.g. by means of filtration); (c) liquid-liquid extraction; (d) simultaneous crystallization and: (e) solid-solid separation.

The feed stream may be any stream comprising the organic compound. The feed stream is a liquid stream and is typically an aqueous stream. The organic compound is typically dissolved in the feed stream (e.g. in water in case of an aqueous stream). In a preferred embodiment, the feed stream is a fermentation stream, which is also typically an aqueous stream. The fermentation stream may for example be a stream that originates from a fermentation process. In such a case, the method of the invention may include a fermentation step, preceding the extraction step, wherein the fermentation stream is formed. Such a fermentation step includes fermentation of a carbon source such as sugars to obtain the organic compound The fermentation stream is typically aqueous and comprises the organic compound to be recovered. For example, the fermentation stream may be a fermentation broth comprising micro-organisms, a carbon source (e.g. sugar), a nutrient (e.g. specific ions needed to get growth of the organism) and one or more fermentation products (e.g. the organic compound to be recovered and possible by-products). The fermentation stream may also be a fermentation product stream. Such a product stream may have already been treated, for example by removing certain waste materials and/or solid material. For example, the fermentation stream may first be subjected to centrifugation or filtration (e.g. microfiltration or ultrafiltration) to remove solid material (e.g. biomass) from the stream before feeding the stream to the extraction step.

The organic compound in the feed stream may be any organic compound that can be produced by micro-organisms in a fermentation reaction. The organic compound can be the main fermentation product formed in the fermentation reaction. For example, the organic compound may be selected from carboxylic acids (in particular monocarboxylic acids and dicarboxylic acids), polyols and cyclic esters (e.g. a lactone). The organic compound may be relatively small, e.g. it may have less than 12 carbon atoms, typically 2-10 carbon atoms. In particular, the organic compound may be selected from the group consisting of 1,4 butanediol, succinic acid, formic acid, malic acid, 2,5-furan dicarboxylic acid, 3-hydroxypropionic acid, aspartic acid, glucaric acid, glutamic acid, itaconic acid, levulinic acid, 3-hydroxybutyrolactone, glycerol, sorbitol, xylitol and arabitol. The organic compound may also be an alcohol, such as an aromatic alcohol, e.g. 2-sec butylphenol.

The organic compound may have a melting point of −50 to +250° C. However, in view of obtaining a mixture having the desired eutectic temperature (see below), the organic compound preferably has a melting point of −10 to +200° C., more preferably 0 to +100° C., even more preferably +10 to +80° C.

According to the method of the invention, the organic compound is extracted from the feed stream into an organic solvent. An advantage of an extraction step is that it provides for an easy way of separating the organic compound from water soluble compounds and/or solid material that may be present in the feed stream. A further advantage of extraction in case of fermentation streams may be that it may reduce possible product inhibition of the organic compound on micro-organisms that may be present in the fermentation stream (for example in case of itaconic acid). It will be evident that the solvent of the feed stream (typically water) and the organic solvent should not dissolve in each other for an effective extraction. In case of an aqueous feed stream, the organic solvent is preferably immiscible with water.

The concentration of organic compound in the feed stream during extraction is not particularly critical and may for example be in the range of 1 wt. % to 30 wt. %, preferably 5 to 20 wt %, based on the total weight of the fermentation stream. The operating temperature at which extraction is conducted may be 0-100° C., in particular 10-80° C., more in particular 20-70° C.

In case of the feed stream being a fermentation stream, the temperature of the feed stream may be chosen close to the temperature used for the fermentation process wherein the organic compound is produced (for reasons of energy efficiency), for example within 20° C. of this temperature. For example, the temperature of the fermentation stream during extraction may be 0-100° C., in particular 10-80° C., more in particular 20-70° C. The organic solvent during extraction may have a temperature similar to the fermentation stream. Accordingly, the temperature of the organic solvent during extraction may also be 0-100° C., in particular 10-80° C., more in particular 20-70° C.

During extraction, the organic solvent is enriched in the organic compound, while the feed stream (e.g. fermentation stream) is at least partially depleted in the organic compound. After extraction, a mixture of the organic compound and the organic solvent is obtained (the extract). The organic compound will typically be dissolved in the organic solvent. The resulting mixture may comprise 1-50 wt. % of the organic compound and 50-99 wt. % of the organic solvent. Further, a raffinate is obtained in the extraction step, which may be a waste stream or can be fed back to fermentation. This may be done with or without further treatment before recycling of the stream in the fermentation.

Thus, as explained above, the extract (i.e. the mixture of the organic compound and the organic solvent) is subjected to simultaneous crystallization. The raffinate may be a wastestream or recycled. The extract and raffinate can be separated from each other (as is common for extraction techniques such as liquid-liquid extraction).

Preferably, the extract of the extraction step, i.e. the mixture of organic compound and organic solvent, is directly fed to the simultaneous crystallization step. There is no need for first subjecting the mixture to one or more evaporation steps, which contributes to the energy efficiency of the method of the invention. When starting simultaneous crystallization, the mixture is preferably a liquid mixture, i.e. a mixture of a liquid organic compound and a liquid organic solvent. By having both components of the mixture in the liquid state, a more effective simultaneous crystallization can be conducted. Furthermore, the organic compound is preferably present in its neutral form when starting simultaneous crystallization. This is for example desirable when the organic compound is a carboxylic acid. When such organic compounds would be present as carboxylate ions, there is a risk that the organic compound is recovered as a salt instead of the neutral product.

Simultaneous crystallization is achieved by cooling, i.e. by lowering the temperature of the mixture. Simultaneous crystallization will occur when the temperature of the mixture is cooled to a sufficiently low temperature, i.e. cooled to the eutectic temperature of the mixture or below. Such a simultaneous crystallization technique is also known under the name eutectic freeze crystallization (EFC). EFC is a technique generally known for recovering salts and ice from a salt solution. Simultaneous crystallization will only occur at a certain ratio of organic compound and organic solvent, viz. the eutectic composition. When cooling the mixture to (or below) its eutectic temperature at a composition other than the eutectic composition, either the organic compound or the organic solvent will crystallize. This will effectively remove this solid component from the liquid mixture. As a result, the ratio of the organic compound and organic solvent will change and come closer to the ratio of the eutectic composition. The step where the composition of the mixture is shifted to the eutectic composition can be done in a separate step preceding the simultaneous crystallization (e.g. in a separate crystallizer) or be conducted in the same crystallizer as in which the simultaneous crystallization takes place. Eventually, the ratio will be equal to that of the eutectic composition. At this point, simultaneous crystallization will occur.

Eutectic freeze crystallization has only been occasionally used in the field of downstream processing of fermentation streams and never in combination with extraction methods. For example, WO 2004/089503 is directed to a process for the recovery and/or purification of an organic compound from a solution comprising a solvent by adjusting the temperature of the solution to a temperature at which both the organic compound and the solvent are at least partially in the solid phase. According to WO 2004/089503, the solution when cooled to or under the eutectic point will in general consist of ice crystals, crystals of at least one organic compound and a liquid. The ice crystals can be separated rather easily due to the low density of ice which will cause the ice to float. WO 2004/089503 further describes the recovery of the protein nisine from a filtrated fermentation broth. The aqueous solution comprising nisine was cooled in the presence of ice flakes.

All specific embodiments and experimental examples disclosed in WO 2004/089503 use water as the solvent. WO 2004/089503 considers the formation of ice crystals to be advantageous, because they can be separated easily due to the well-known low density of ice which will cause the ice to float. However, the inventors realized that using water also has the disadvantage of high energy costs due to cooling, because simultaneous crystallization will only occur at temperatures below 0° C.

Furthermore, the phase diagram organic compound-water is strongly dependent on the melting temperature of the pure organic compound. Especially for organic compounds with a melting point below +100° C., the eutectic temperature of the water/organic compound mixture tends to become far below 0° C. Furthermore, the eutectic composition tends to move to such high concentrations of the organic compound that eutectic freeze crystallization becomes practically and economically unfavorable due to the need of first having to crystallize the majority of water from the water/organic compound mixture.

Unless specified otherwise, the eutectic temperature as used herein refers to the temperature that corresponds with the specific eutectic point of the mixture at which simultaneous crystallization of the organic solvent and the organic compound starts to occur. According to the method of the invention, simultaneous crystallization is achieved by cooling the mixture to a sufficiently low temperature, i.e. below the eutectic temperature of this specific eutectic point. This is not affected by the mixture possibly having more than one eutectic point, e.g. due to the presence of other compounds in the mixture. The eutectic temperature of the mixture may be in the range of −30 to +80° C., preferably in the range of −10 to +60° C., more preferably in the range of 0 to +40° C. Such relatively mild temperatures are desirable, because it will provide for an overall more energy efficient process (as these temperatures are relatively close to fermentation temperatures and can be achieved by standard methods and equipment for cooling). The eutectic point of many mixtures are known. However, if the eutectic point is not known, the skilled person will be able to make a rough estimate of the eutectic point based on the melting points of the organic solvent and the organic compound or by using theoretical equations like the van 't Hoff equation to simulate the phase diagram. Furthermore, the skilled person may determine the eutectic point by standard methods for experimental screening.

In view of the above, the mixture is typically cooled to a temperature of −20 to 80° C., preferably to −10 to 60° C., more preferably to 0 to 40° C. The eutectic temperature may not be the fixed operating temperature of the simultaneous crystallization as the eutectic temperature may shift due to the presence of impurities and/or other components in the mixture. Typically the operating temperature of the simultaneous crystallization may be up to 30° C., more preferably 20° C. and even more preferably less than 10° C. below the eutectic temperature.

Simultaneous crystallization thus results in a mixture of the organic compound in solid form (solid organic compound), the organic solvent in solid form (solid organic solvent) and typically also one or both of the organic compound and organic solvent in liquid form. The liquid components of the mixture may be referred to as the mother liquor.

After simultaneous crystallization, the organic compound is recovered by separating the solid organic solvent and solid organic compound. The inventors further found that the solid organic compound and the solid organic solvent obtained by simultaneous crystallization can generally be easily separated, e.g. based on differences in density between the organic compound and the organic solvent. Despite the difference in density being relatively small (in particular compared to the difference when water would have been used as the solvent), the organic compound and the organic solvent were found to be surprisingly easy and efficient to separate. As a result of the efficient separation, both the compound and the solvent have a good purity. The organic solvent can be recycled (typically after melting) to the liquid-liquid extraction. Thus, the method of the invention has the advantage that the solvent and product can be efficiently recovered, without requiring complex and/or energy consuming downstream processing steps such as back-extraction and/or evaporation.

In case the solid organic solvent and solid organic compound are separated based on their difference in density, separation may for example be conducted by gravity settling, and/or flotation or by centrifugation or by any other known technique making use of the difference in density. The solid organic solvent and solid organic compound can also be separated based on the particle size of the two types of crystals. In this case, techniques like filtration or sieving may be used as the separation technique.

As explained above, the solid organic compound and solid organic solvent are separated from each other by solid-solid separation techniques. After or during separation, the solid organic compound can be removed from the mixture formed in the simultaneous crystallization. The solid organic solvent and the mother liquor can be recycled in the method of the invention. For example, solid organic solvent may be melted and used in the extraction step. Liquid organic solvent present in the mother liquor may also be reused in the extraction step. Liquid and/or solid organic compound can be recycled in the simultaneous crystallization step. The liquid and/or solid organic compound may be added to the mixture of the organic solvent and the organic compound, before or during cooling of said mixture in the simultaneous crystallization step.

After separation, the solid organic compound crystals may be subjected to one or more purification steps. However, purification will require relatively less units of operation since the quality of the solid organic compound crystals leaving the separation process will already be high and the amount of solvent and other components is relatively low.

An important aspect of the method of the invention is the choice for performing simultaneous crystallization on a mixture comprising two organic compounds, i.e. the organic compound to be recovered and the organic solvent. This is not an obvious choice for several reasons. First, fermentation streams are typically aqueous. Therefore, transferring the organic compound to an organic solvent appears to complicate the process by adding an additional step when trying to recover the organic compound by eutectic freeze crystallization. Second, efficient regeneration of the organic solvents and recovery and further purification of the organic product is often difficult and energy-consuming. Therefore, it is not obvious to extract the organic compound into an organic solvent when not absolutely necessary. Third, as discussed above, water forms low-density ice crystals during simultaneous crystallization, which is very desirable with respect to the subsequent separation step and which points at trying to achieve eutectic crystallization directly from the aqueous fermentation stream.

However, the inventors realized that by first extracting the organic compound into an organic solvent, it is possible to extend the operating and application window for eutectic freeze crystallization significantly. For example, the method of the invention enables operation of eutectic freeze crystallization at much more favorable conditions such as more desirable temperature ranges (e.g. above 0° C.) and more desirable eutectic compositions (and thus desirable concentrations of the organic product in the solvent). The ability to apply eutectic freeze crystallization in other solvents than water creates an extra degree of freedom while it also presents simpler and better routes than the conventional extraction-back extraction routes. For example, the eutectic temperature of the mixture to be simultaneously crystallized can be influenced by selecting a suitable organic solvent. In this way, the eutectic temperature may be adjusted to a desirable temperature that lies close to the temperature of the fermentation stream. Thus, the decrease in temperature required for simultaneous crystallization can be small, which is desirable with respect to the energy consumption of the method.

Accordingly, when trying to recover a certain organic compound, it will be necessary to select a suitable organic solvent. In view of the above, it will be understood that the choice for a suitable organic solvent amongst others depends on the effect it has on the eutectic temperature of the mixture with the organic compound. The following criteria can be used for selecting a suitable organic solvent: (1) the organic solvent is preferably liquid at the operating temperature of the extraction step; (2) the organic solvent preferably has a solidification temperature close to the operating temperature of the extraction (this temperature corresponds to the melting point for the organic solvent described below); (3) the solvent preferably has limited solubility in water, e.g. less than 100 g/kg water, preferably less than 10 g/kg water and even more preferably less than 1 g/kg water; (4) water preferably does not dissolve in large quantities in the organic solvent, e.g. less than 200 g/kg organic solvent, preferably less than 20 g/kg solvent and even more preferably less than 2 g/kg solvent; (5) the distribution or partitioning coefficient should preferably be such that extraction immediately leads to a mixture with a composition close to the eutectic composition. In general, it is considered to be advantageous when the eutectic composition is situated at a relatively low concentration of the organic compound, such as to avoid the need for crystallizing large amounts of organic solvent in the mixture before reaching the eutectic point. The solvent may fulfill at least one of the five criteria mentioned above, but preferably more. In principle, any combination of two, three, four or five of the above criteria may be used to provide a suitable solvent).

In this respect, it was found that the melting point of the organic solvent and the organic compound has significant influence on the eutectic point of the mixture. Therefore, the organic solvent is preferably selected such as to have a melting point that lies close to the desired eutectic temperature. In principle, the organic solvent may have a melting point of −50 to 250° C. However, in view of the preferred temperatures for the eutectic temperature already mentioned above and in view of the liquid-liquid extraction conducted prior to the simultaneous crystallization, the organic solvent preferably has a melting point of −10 to +100° C., more preferably +10 to +80° C., even more preferably +20 to +60° C.

Accordingly, the organic solvent may be selected from the group consisting of trialkylphosphine oxides, dialkylsulfoxides, aliphatic hydrocarbons, aromatic hydrocarbons, alcohols, carboxylic acids and esters, in particular those with a melting point in the above-defined ranges. For example the organic solvent may be tri-n-octylphosphine oxide (melting point of 50-54° C.), dimethylsulfoxide (melting point of 19° C.), p-xylene (melting point of 13° C.), 1-octanol (melting point of −16° C.), acetic acid (melting point of 16-17° C.), t-butyl alcohol (melting point of 25-26° C.) or dioxane (melting point of 12° C.).

Trialkylphosphine oxides and dialkylsulfoxides were found to be particularly desirable as the organic solvent used in the method of the invention, in particular in view of simultaneous crystallization and subsequent separation. Both groups are expected to be very suitable for use in the method of the invention when recovering an alcohol (e.g. 1,4 butanediol) or carboxylic acid (e.g. itaconic acid).

Trialkylphosphine oxide is a group of compounds with the formula $O=P(R)_3$, wherein R is an alkyl group. The alkyl group is preferably a $C_{1-20}$ alkyl, preferably a $C_{4-12}$ alkyl, more preferably a $C_{6-10}$ alkyl. Particular good results were obtained using tri-n-octylphosphine oxide (TOPO) as the organic solvent.

Dialkylsulfoxide is a group of compounds with the formula $O=S(R)_2$, wherein R is an alkyl group. The alkyl group is preferably a $C_{1-8}$ alkyl, preferably a $C_{1-6}$ alkyl, for example dimethylsulfoxide (DMSO) or dibutylsulfoxide (DBSO).

The eutectic point of a mixture depends both on the type of organic compound and organic solvent used, in particular on their melting points. Therefore, the choice for a suitable organic solvent may vary depending on the specific organic compound that is to be recovered. Accordingly, certain combinations of organic compounds and organic solvents may be preferred.

Particular good results have been obtained using TOPO as the organic solvent and alcohols or carboxylic acids as the organic compound. For example, TOPO and 1,4 butanediol form a mixture having a eutectic temperature of 16° C. Using this combination, crystallization can be obtained at temperatures just below room temperature which can easily be achieved with standard cheap options for cooling. Another example is TOPO and itaconic acid, which form a mixture having a eutectic temperature of about 20° C.

Figure 2:
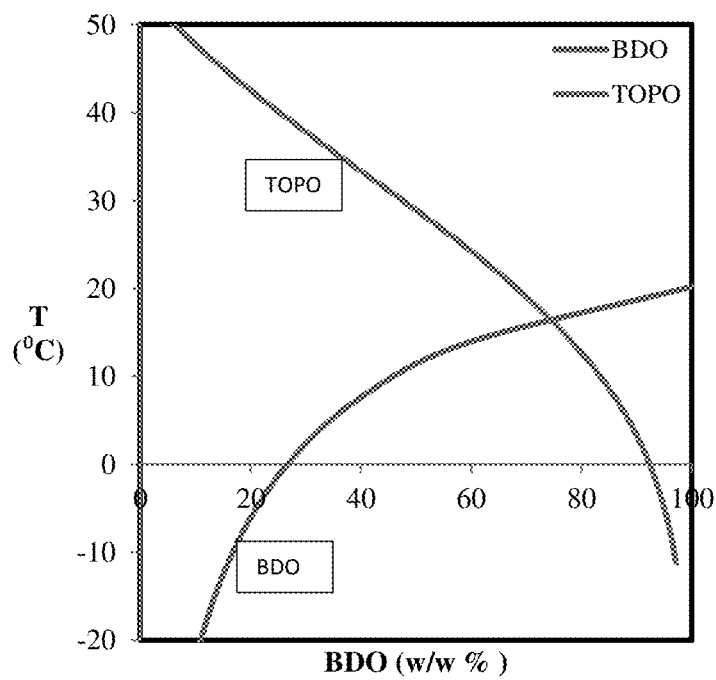
FIG. 2 shows the theoretical phase diagram of a mixture of 1,4 butanediol and tri-n-octylphosphine oxide.

The skilled person will be able to derive the information on the eutectic temperature and eutectic composition of a mixture of an organic solvent and an organic compound from the phase diagram of the mixture, wherein the equilibrium crystallization temperatures, the points at which the first crystals are formed, of mixtures of both compounds are plotted against the composition of the mixture (i.e. ranging from 0 to 100 wt. % organic compound). FIG. 2 is an example of such a theoretical phase diagram for a mixture of 1,4 butanediol and TOPO.

As said before the text introduces the principle of the invention using fermentation as example. The skilled person will recognize that the principle of the invention can also be applied in any processes where an organic compound in an aqueous stream is extracted with an organic solvent. An illustrative, but non-limitative example in this category, is the treatment of aqueous process and waste water streams. Also these streams are often diluted and sometimes also complex multi-component solutions. The purpose of the liquid-liquid extraction is then to selectively remove an organic component from such a stream. Examples are removal of impurities or by-products from process streams or the removal of toxic impurities in waste water treatment like the removal of aromatics in order to make the waste water suited for biological treatment. The recovery of the extracted compound (and the regeneration of the solvent) is also important in the given examples for reasons of material and cost efficiency, to enable recycling of the solvent and the organic compound or to reduce the costs for waste disposal. Obviously, the described invention can also be applied on the afore-mentioned streams and applications and it will generate the same kind of advantages as described in more detail for the example of extracting an organic compound or product from a fermentation stream.

In another aspect, the invention is directed to a mixture comprising crystals of a first organic compound, crystals of a second organic compound different and at least 25 wt. % of the first or second organic compound in liquid form. Such a mixture is obtainable by the simultaneous crystallization step conducted in the method of the invention. The first organic compound may correspond to the organic compound as defined above, while the second organic compound may correspond to the organic solvent as defined above. The combined amount of crystals of the first and second organic compound in the mixture may be 10-50 wt. %, preferably 20-25 wt. %, based on the total weight of the mixture. Such an amount is suitable for the separation step conducted in the method of the invention. The mixture may comprise 50-90 wt. %, preferably 75-80 wt. % of the first and second organic compound or the organic solvent in liquid form. The mixture may comprises at least 1 wt. %, preferably at least 3 wt. % of both the first and second organic compound crystals, based on the total weight of the mixture. The crystals obtained in simultaneous crystallization are typically one-component crystals. This means disregarding any impurities, the crystals in the mixture consist only of one compound, i.e. the first or second organic compound. Accordingly, the first organic compound crystals may consist of at least 90 wt. %, preferably at least 95 wt. % organic compound, based on the total weight of the first organic compound crystals. The second organic compound crystals may consist of at least 90 wt. %, preferably at least 95 wt. % organic solvent, based on the total weight of the second organic compound crystals.

The invention will be further illustrated by the following experimental examples.

Example 1: Simultaneous Crystallization of BDO and TOPO

A mixture of 1,4 butanediol (BDO) an tri-n-octyl phosphine oxide (TOPO) was gradually cooled to a temperature below 16° C. (i.e. below the eutectic temperature of the mixture), which induced crystallization in the mixture.

A sample of the mixture comprising crystals was taken and analyzed under a microscope. Two types of crystals were observed: the first had a needle-like shape, the other had a snow like structure.

The temperature of the sample was then increased above the eutectic temperature and the snow like crystals melted, while the needle-like crystals remained.

The crystals were removed from the mixture and their melting temperature was measured to be 55° C., which corresponds to the melting point of TOPO.

The mixture was then seeded with end crystals of BDO to initiate crystallization. The resulting crystals were again analyzed under the microscope. The crystals had a shape of elongated tubes, which was different than the needle-like shape observed for the TOPO crystals. Therefore, it was concluded that these crystals must be BDO crystals.

The experiment shows the proof of concept for eutectic freeze crystallization of a TOPO-BDO mixture.

Example 2: Simultaneous Crystallization of IA in H₂O and TOPO

This example illustrates the energy efficiency of using organic solvents in eutectic freeze crystallization compared to the solvent being water.

The binary phase diagram of Itaconic Acid/Water was determined both experimentally and theoretically:

1. Theory: The melting points were calculated using the Van't Hoff equation under standard conditions.
2. Experimental (Crystal16 method): Liquid mixtures of water and itaconic acid with varying amounts of itaconic acid (1-15 wt. %) were prepared. The crystallization points of the different mixtures were experimentally determined by cooling a 1 mL sample of each of the mixtures in a parallel crystallizer (Crystal16, Technobis Group). The melting point was the highest temperature at which solid material started to form.
3. Experimental: Two similar experiment as described in 2 were conducted with 100 mL samples of mixtures comprising 20 wt. % IA and 10 wt. % IA respectively, using a 100 mL crystallizer set-up. The difference between this method and the Crystal16 method illustrates the effect of scaling.

The results of determining the IA crystallization point using the above three methods are shown in Table 1.

TABLE 1

Crystallization Point of IA/water mixture

| IA/Water content | Crystallization Temperature (° C.) | | |
| --- | --- | --- | --- |
| | Theory (1) | Experimental (2) | Experimental (3) |
| 20 wt. % IA | 48 | — | 47.85 |
| 15 wt. % IA | 40 | 38 | — |
| 10 wt. % IA | 28 | 28 | 29.28 |
| 3 wt. % IA | 4 | 1 | — |
| 1 wt. % IA | −0.5 | 1 | — |

Figure 3:
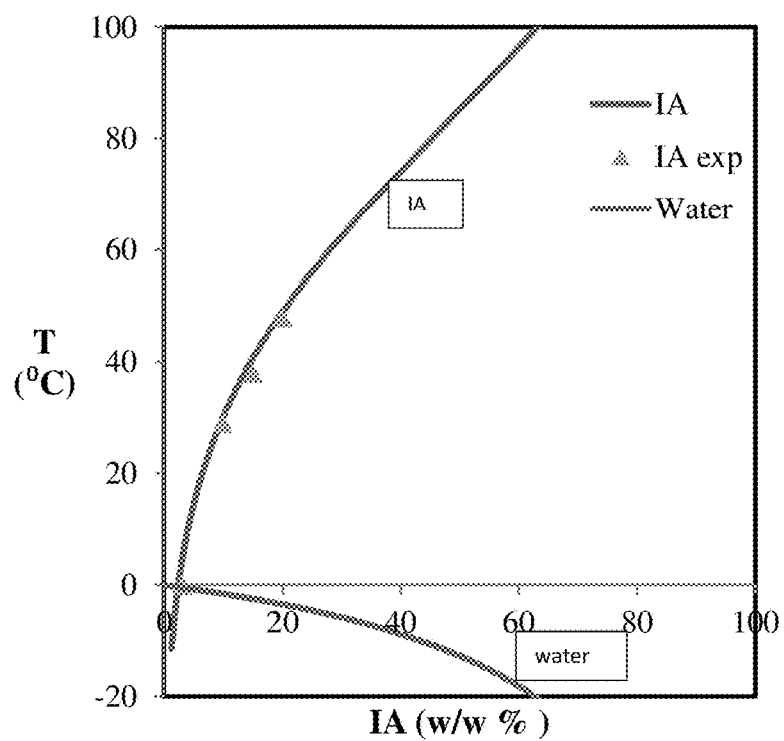
FIG. 3 shows the binary phase diagram of a mixture of water and itaconic acid.

The calculated and experimental values were roughly the same. Further, scaling of the experiment did not seem to have a large effect on the crystallization point. The data on the crystallization point of IA was combined with experimental data of the crystallization point of water in the mixture. From these combined data, the binary phase diagram was plotted, which is shown in FIG. 3. The eutectic point can be found at the intersection of the two lines. The eutectic point was calculated to be 2.4 wt. % itaconic acid at −05° C.

The above experiment was repeated for mixtures of itaconic acid and tri-n-octyl phosphine oxide (TOPO). The results are shown in Table 2.

TABLE 2

Crystallization Point of IA/TOPO mixture

| IA/TOPO content | Crystallization Temperature (° C.) | |
| --- | --- | --- |
| | Theory (1) | Experimental (2) |
| 1 wt. % IA | 53 | 48.9 |
| 2.4 wt. % IA | 64 | 54.3 |
| 3.8 wt. % IA | 81 | 52.6 |
| 5.3 wt. % IA | 88 | 51.4 |
| 7 wt. % IA | 98 | 49.6 |
| 8.5 wt. % IA | 103 | 46.5 |
| 10 wt. % IA | 107 | 42.0 |
| 12 wt. % IA | 115 | 36.0 |
| 13.3 wt. % IA | 117 | 27.0 |
| 14 wt. % IA | 118 | 23.1 |
| 15 wt. % IA | 120 | 25.0 |
| 16.7 wt. % IA | 129 | 98.0 |

Figure 4:
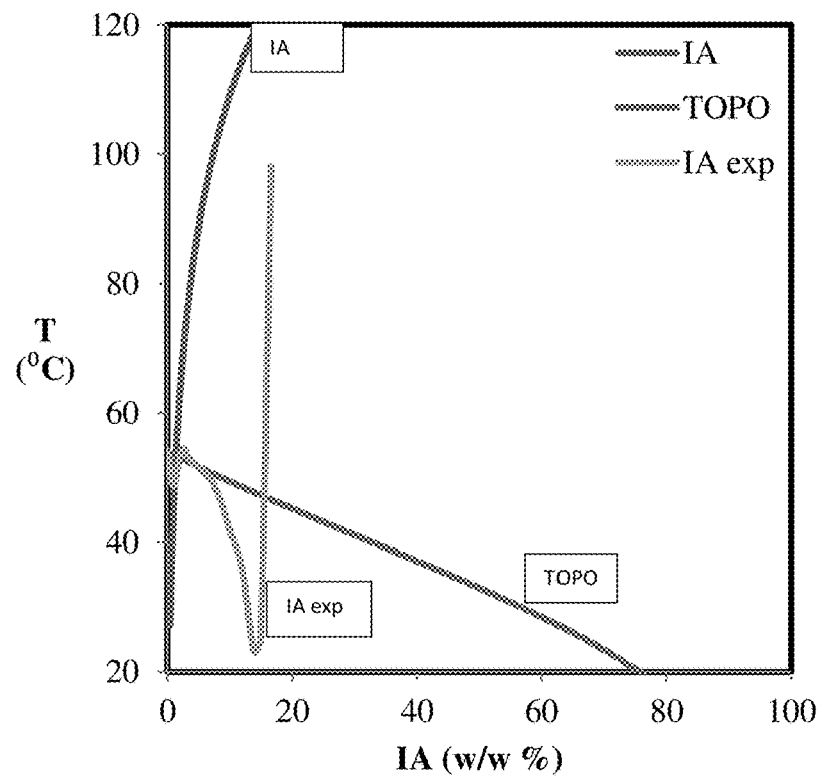
FIG. 4 shows the binary phase diagram of a mixture of itaconic acid and tri-n-octyl phosphine oxide.

An important difference between calculated and experimental data was observed. FIG. 4 shows the binary phase diagram of IA/TOPO with both the theoretical data (upper left line) and the experimental data (line with minimum of about 18° C.). Based on the experimental data, it can be concluded that crystallization of the mixture may already start at 14.2 wt % itaconic acid at around 21° C.

This Example shows that using TOPO instead of water increases the eutectic temperature from −0.5° C. to 21° C. in a IA/TOPO mixture. The eutectic temperature of TOPO near room temperature makes it an excellent solvent for energy efficient eutectic freeze crystallization as conducted in the method of the invention.

Example 3: Separation of IA and TOPO Crystals

Figure 5:
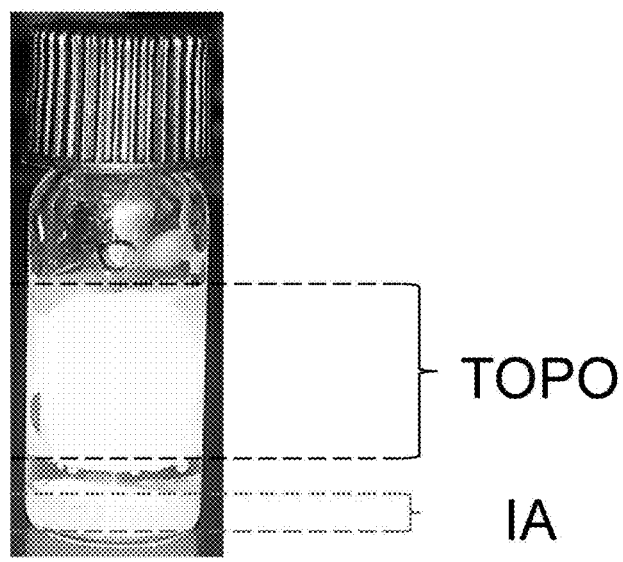
FIG. 5 shows a photograph of a vial containing a mixture of itaconic acid and tri-n-octyle phosphine oxide.

A mixture of itaconic acid (IA) and tri-n-octyl phosphine oxide (TOPO) was prepared. The IA content in the mixture was chosen close to the eutectic point of 14.2 wt. %, as determined in Example 2. A vial was filled with this mixture. The temperature of the mixture was brought below 21° C. and the formation of crystals was analyzed. After crystallization, the crystals of IA were found at the bottom, while crystals of TOPO were found at the top of the vial. A photograph was taken of the vial, which is shown in FIG. 5.

It can be concluded from this experiment that TOPO crystals have a lower density than IA crystals and that the difference in density is sufficient to cause an effective separation of the two crystal types. This will make it easy to separate the two crystal layers without having to consume much energy.

Example 4: Simultaneous Crystallization of BDO and TOPO

The experiments described in Example 2 were repeated for mixtures of 1,4 butanediol and tri-n-octyl phosphine oxide (TOPO). The results are shown in Table 3.

TABLE 3

Crystallization Point of BDO/TOPO mixture

| BDO/Water content | Crystallization Temperature (° C.) | | |
| --- | --- | --- | --- |
| | Theory (1) | Experimental (2) | Experimental (3) |
| 2 wt. % BDO | 53 | 53.1 | — |
| 10 wt. % BDO | 48 | 43.1 | 42.2 |
| 19 wt. % BDO | 37.5 | 31.8 | 33 |
| 25 wt. % BDO | 40 | 25.9 | 25 |

TABLE 3-continued

Crystallization Point of BDO/TOPO mixture

| | Crystallization Temperature (° C.) | | |
|---|---|---|---|
| BDO/Water content | Theory (1) | Experimental (2) | Experimental (3) |
| 40 wt. % BDO | 33 | 16.3 | 16 |
| 59 wt. % BDO | 25 | 18.6 | — |
| 65 wt. % BDO | 22 | 20.0 | — |
| 75 wt. % BDO | 17 | 19.7 | — |
| 85 wt. % BDO | 18 | 20.2 | — |
| 90 wt. % BDO | 18.5 | 21.0 | — |

Figure 6:
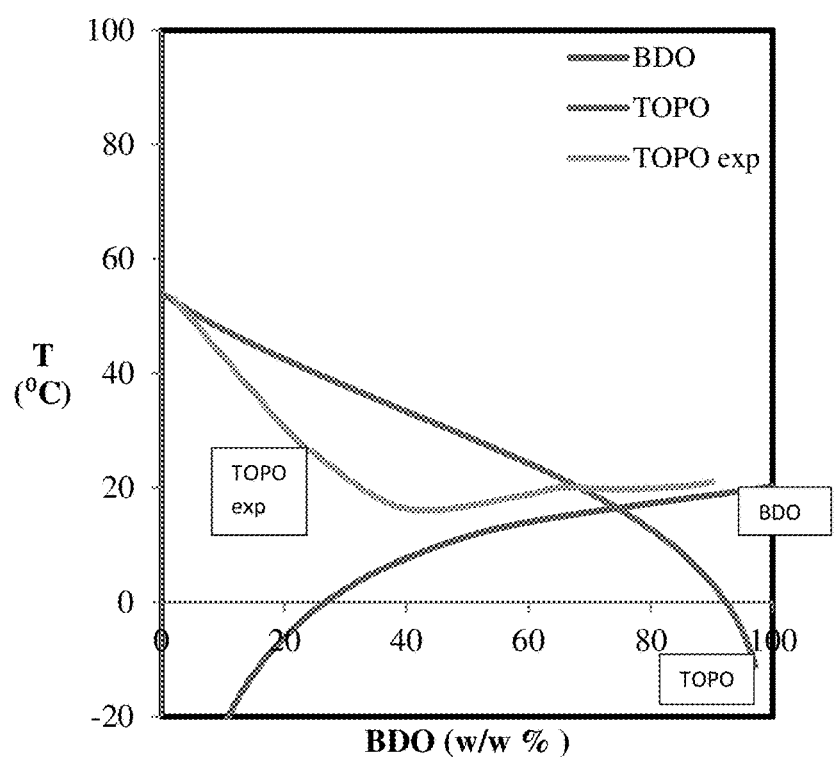
FIG. 6 shows the binary phase diagram of a mixture of 1,4 butanediol and tri-n-octyl phosphine oxide.

The binary phase diagram of TOPO-1,4-butanediol, is given in FIG. 6, where the curved middle line corresponds to the experimental results.

The data shown in FIG. 6 shows that the experimental results do not correspond to the calculated values. Based on the experimental results, it can be concluded that crystallization of the mixture starts at 16° C. at 40 wt % TOPO-1,4-butanediol.concentration. The theoretical values indicated that the eutectic point would be at 16.4° C. at 74.5 wt % composition.

Furthermore, the theoretical binary phase diagram of a 1,4-butanediol/water mixture was calculated. The eutectic point was determined at −28.4° C. at 64.3 wt. % BDO. Cooling to a temperature far below zero to achieve simultaneous crystallization will give rise to high energy costs. Therefore, the calculated value gives a good indication of the energy savings that can be obtained by using TOPO instead of water as the solvent.

This Example shows that the eutectic temperature of BDO/TOPO mixtures are is at 16° C., i.e. close to room temperature. The eutectic temperature of TOPO near room temperature makes it an excellent solvent for energy efficient eutectic freeze crystallization as conducted in the method of the invention.

Example 5: Liquid-Liquid Extraction

Experiments were conducted to conduct liquid-liquid extraction from water into TOPO. TOPO was not miscible with water. The inventors found that TOPO could easily extract organic compounds such as BDO or IA from a water phase.

The invention claimed is:

1. Method for recovering an organic compound from a liquid feed stream comprising the steps of:
   a liquid-liquid extraction, wherein the organic compound is extracted from the feed stream into an organic solvent, thereby obtaining an extract, which is a mixture of the organic solvent and the organic compound;
   simultaneously crystallizing the solvent and the organic compound by cooling said mixture; and
   a solid-solid separation step to separate the solid solvent and solid organic compound, wherein the organic compound is selected from the group consisting of carboxylic acids, alcohols and cyclic esters.

2. Method according to claim 1, wherein the solid solvent and solid organic compound are separated based on their difference in density or size.

3. Method according to claim 1, wherein the solid solvent and solid organic compound are separated by gravity settling, flotation, hydrocyclones, or centrifugation.

4. Method according to claim 1, wherein the solvent and the organic compound are simultaneously crystallized by cooling the mixture to a temperature equal to or lower than the eutectic temperature of the mixture.

5. Method according to claim 1, wherein the organic compound is selected from the group consisting of 1,4-butanediol, succinic acid, formic acid, malic acid, 2,5-furan dicarboxylic acid, 3-hydroxypropionic acid, aspartic acid, glucaric acid, glutamic acid, itaconic acid, levulinic acid, 3-hydroxybutyrolactone, glycerol, sorbitol, xylitol and arabitol.

6. Method according to claim 1, wherein the organic solvent has a melting point in the range of +10 to +100° C.

7. Method according to claim 1, wherein the organic solvent is selected from the group consisting of trialkylphosphine oxides, dialkylsulfoxides, aliphatic hydrocarbons, aromatic hydrocarbons, alcohols, carboxylic acids and esters.

8. Method according to claim 1, wherein the mixture has a eutectic temperature in the range of −20 to +80° C.

9. Method according to claim 1, wherein the stream is a fermentation stream.

10. Method according to claim 1, wherein the method further comprises the step of fermenting a carbon source to obtain the organic compound.

11. Method according to claim 1, wherein the liquid feed stream is an aqueous stream.

12. Method according to claim 1, wherein the organic compound is 1,4-butanediol or itaconic acid; and wherein the organic solvent is tri-n-octylphosphine oxide.

13. Mixture comprising at least 1 wt. % crystals of a first organic compound, at least 1 wt. % crystals of a second organic compound different than the first compound and at least 25 wt. % of the first or second organic compound in liquid form, based on the total weight of the mixture.

14. Mixture obtainable by the simultaneous crystallization step as defined in claim 1.

15. Mixture according to claim 13, wherein the combined amount of crystals of the first and second organic compound is 10-50 wt. %, based on the total weight of the mixture.

16. Mixture according to claim 13, wherein the first compound is 1,4-butanediol or itaconic acid; and wherein the second compound is tri-n-octylphosphine oxide.

17. Method for recovering an organic compound from a liquid feed stream comprising the steps of:
   a liquid-liquid extraction, wherein the organic compound is extracted from the feed stream into an organic solvent, thereby obtaining an extract, which is a mixture of the organic solvent and the organic compound;
   simultaneously crystallizing the solvent and the organic compound by cooling said mixture; and
   a solid-solid separation step to separate the solid solvent and solid organic compound, wherein the organic solvent is a trialkylphosphine oxide or dialkylsulfoxide.

18. Method according to claim 17, wherein the solid solvent and solid organic compound are separated based on their difference in density or size.

19. Method according to claim 17, wherein the solid solvent and solid organic compound are separated by gravity settling, flotation, hydrocyclones, or centrifugation.

20. Method according to claim 17, wherein the solvent and the organic compound are simultaneously crystallized by cooling the mixture to a temperature equal to or lower than the eutectic temperature of the mixture.

21. Method according to claim 17, wherein the organic compound has a melting point in the range of −50 to +250° C.

22. Method according to claim 17, wherein the organic solvent is selected from tri-n-octylphosphine oxide (TOPO), dimethylsulfoxide (DMSO), and dibutylsulfoxide (DBSO).

23. Method according to claim 17, wherein the mixture has a eutectic temperature in the range of −20 to +80° C.

24. Method according to claim 17, wherein the stream is a fermentation stream.

25. Method according to claim 17, wherein the method further comprises the step of fermenting a carbon source to obtain the organic compound.

26. Method according to claim 17, wherein the liquid feed stream is an aqueous stream.

* * * * *